(12) United States Patent
Tamiz

(10) Patent No.: US 8,785,374 B2
(45) Date of Patent: Jul. 22, 2014

(54) INHIBITORS OF MAMMALIAN TIGHT JUNCTION OPENING

(75) Inventor: Amir Tamiz, Silver Spring, MD (US)

(73) Assignee: Alba Therapeutics Corporation, Baltimore, MD (US)

( * ) Notice: Subject to any disclaimer, the term of this patent is extended or adjusted under 35 U.S.C. 154(b) by 1129 days.

(21) Appl. No.: 12/738,815

(22) PCT Filed: Oct. 20, 2008

(86) PCT No.: PCT/US2008/080491
§ 371 (c)(1),
(2), (4) Date: Dec. 15, 2010

(87) PCT Pub. No.: WO2009/052489
PCT Pub. Date: Apr. 23, 2009

(65) Prior Publication Data
US 2011/0077191 A1    Mar. 31, 2011

Related U.S. Application Data

(60) Provisional application No. 60/981,399, filed on Oct. 19, 2007.

(51) Int. Cl.
*A61K 38/00* (2006.01)
*A61K 36/42* (2006.01)

(52) U.S. Cl.
USPC .............. 514/1.5; 514/1.7; 514/2.2; 514/7.3; 530/330; 530/331

(58) Field of Classification Search
None
See application file for complete search history.

(56) References Cited

U.S. PATENT DOCUMENTS

| | | | |
|---|---|---|---|
| 8,299,017 B2 * | 10/2012 | Paterson et al. | 514/1.1 |
| 2002/0115825 A1 | 8/2002 | Fasano | |
| 2004/0009956 A1 | 1/2004 | Pei et al. | |
| 2005/0261196 A1 | 11/2005 | Turner et al. | |
| 2006/0287233 A1 | 12/2006 | Fasano et al. | |

OTHER PUBLICATIONS

International Search Report issued in International Application No. PCT/US2008/080492 on Apr. 29, 2009, 5 pages.

* cited by examiner

*Primary Examiner* — James H Alstrum Acevedo
*Assistant Examiner* — Li Lee
(74) *Attorney, Agent, or Firm* — Cooley LLP

(57) ABSTRACT

The present invention provides novel peptides that inhibit and/or reduce the opening of mammalian tight junctions, i.e. peptide tight junction antagonists. The present invention also provides methods for the treatment of excessive or undesirable permeability of a tissue by administering to a subject suffering from such a condition a composition comprising a peptide tight junction antagonist of the invention.

14 Claims, 2 Drawing Sheets

INHIBITORS OF MAMMALIAN TIGHT JUNCTION OPENING

This application is a National Stage of PCT/US08/80491, filed Oct. 20, 2008, which claims the benefit of U.S. Provisional Application No. 60/981,399, filed Oct. 19, 2007, each of which are hereby incorporated by reference in their entirety.

BACKGROUND

The tight junctions (tj) or zonula occludens (ZO) are one of the hallmarks of absorptive and secretory epithelia (Madara, J. Clin. Invest., 83:1089-1094 (1989); and Madara, Textbook of Secretory Diarrhea Eds. Lebenthal et al, Chapter 11, pages 125-138 (1990)). Tight junctions act as a barrier between apical and basolateral compartments, selectively regulating the passive diffusion of ions and water-soluble solutes through the paracellular (between cells) pathway (Gumbiner, Am. J. Physiol., 253 (Cell Physiol. 22):C749-C758 (1987)). This barrier maintains any gradient generated by the activity of pathways associated with the transcellular route (Diamond, Physiologist, 20:10-18 (1977)).

Variations in transepithelial conductance can usually be attributed to changes in the permeability of the paracellular pathway, since the resistances of enterocyte plasma membranes are relatively high (Madara, supra). The ZO represents the major barrier in this paracellular pathway, and the electrical resistance of epithelial tissues seems to depend on the number of transmembrane protein strands, and their complexity in the ZO, as observed by freeze-fracture electron microscopy (Madara et al, J. Cell Biol., 101:2124-2133 (1985)).

Tight Junction Dysfunctions

Tight junction dysfunction occurs in a variety of clinical conditions, including food allergies, infections of the gastrointestinal tract, autoimmune diseases, Celiac disease and inflammatory bowel diseases (Fasano, A., Pathological and therapeutical implications of macromolecule passage through the tight junction. In Tight Junctions, CRC Press, Inc., Boca Raton, Fla. 697-722 (2001)). Healthy, mature gut mucosa with its intact tight junction serves as the main barrier to the passage of macromolecules. During the healthy state, small quantities of immunologically active antigens cross the gut host barrier. These antigens are absorbed across the mucosa through at least two pathways. Up to 90% of the absorbed proteins cross the intestinal barrier via the transcellular pathway, followed by lysosomal degradation that converts proteins into smaller, non-immunogenic peptides. These residual peptides are transported as intact proteins through the paracellular pathway, which mediates a subtle, but sophisticated, regulation of intercellular tight junction that leads to antigen tolerance.

When the integrity of the tight junction system is compromised, in premature infants or after exposure to radiation, chemotherapy, or toxins, a deleterious immune response to environmental antigens, resulting in autoimmune diseases and food allergies, may be elicited. In normal bowels, the immune reaction is regulated to maintain homeostasis of the gut.

Celiac disease (CD) is a chronic autoimmune disease that is HLA-DQ2/DQ8 haplotype restricted. Gluten, the major protein fraction of wheat, and related proteins in rye and barley are the triggering agents of the disease. Ingested gluten or its derivative fractions (gliadin and subunits) elicit a harmful T cell-mediated immune response after crossing the small bowel epithelial barrier, undergoing deamidation by tissue transglutaminase (tTG) and engaging class II MHC molecules. When the integrity of the tight junction system is compromised, as in CD, a paracellular leak ("leaky gut") and an inappropriate immune response to environmental antigens (i.e., gluten) may develop.

Inflammatory bowel disease (IBD) is a phrase used to describe an inappropriate immune response that occurs in the bowels of affected individuals. Two major types of IBD have been described: Crohn's disease and ulcerative colitis (UC). Both forms of IBD show abnormal profiles of T cell-mediated immunity. In the gut of a person with Crohn's disease a strong Th1 reaction is induced; the Th2 response is upregulated in the colon of a UC sufferer.

The barrier function of the intestines is impaired in IBD. For example, Crohn's disease is associated with increased permeability of the intestinal barrier even in quiescent patients (Oshitani, et al., Int. J. Mol. Med. 15(3):407-10 (2005)). A TNF-α-induced increase in intestinal epithelial tj permeability has been proposed to be an important proinflammatory mechanism contributing to intestinal inflammation in Crohn's disease and other inflammatory conditions (see Ye, et al., Am. J. Physiol.-Gastro. and Liver Physiol., 290(3):496-504 (2006)). Increased intestinal permeability during episodes of active disease correlates with destruction or rearrangement of the tight junction protein complex (Willemsen, et al., Clin. Exp. Immunol. 142(2): 275-284 (2005)).

Acute Respiratory Distress Syndrome (ARDS) presents in about 150,000 individuals in the US annually, with a mortality rate of 30-50%. ARDS occurs in response to diverse forms of severe injury, in which lung edema results in respiratory failure. The current standard of care for ARDS is limited to the management of the disease through supportive mechanical ventilation. The loss of endothelial barrier integrity is central to the pulmonary edema that occurs in ARDS.

Triggering causes for ALI (Acute Lung Injury) including ARDS can, for example, be diffuse pulmonary infections (e.g. due to viruses, bacteria, fungi), aspiration of liquids (e.g. gastric juice or water), inhalation of toxins or irritants (e.g. chlorine gas, nitrogen oxides, smoke), direct or indirect trauma (e.g. multiple fractures or pulmonary contusion), systemic reactions to inflammations outside the lung (e.g. hemorrhagic pancreatitis, gram-negative septicemia), transfusions of high blood volumes or alternatively after cardiopulmonary bypass.

The pulmonary vascular endothelium lines the intravascular space and presents a selective barrier that actively regulates paracellular movement of circulating fluid, macromolecules, and cells, into extravascular tissues and compartments. Loss of this endothelial barrier integrity is the central defect found in acute lung injury (ALI) and ARDS. The host response to a wide range of injurious stimuli includes the biosynthesis and release of endogenous mediators, some of which can open the paracellular pathway in lung microvascular endothelia. Several of these mediators have been identified, including tumor necrosis factor α, interleukin-1, thrombospondin-1, and SPARC/osteonectin, and established as factors that disrupt endothelial barrier integrity. In recent preliminary studies, we found that ΔG, the active domain of zonula occludens toxin (ZOT) of *Vibrio cholerae*, increases paracellular permeability across human lung microvascular endothelial cells (HMVEC-Ls).

Disruption of lung tight junction function has been implicated in the development of allergic sensitization and asthma. In order for an allergen to reach antigen-presenting cells and induce an immune response, such as in asthma, the allergen must cross the lung epithelium. It has been shown that dust mite allergen Der p 1 causes disruption of lung tight junction structure and an increase in the permeability of lung epithelia. Wan, et al. *J. Clinical Investigation* 104(1):123-133 (1999). It was suggested that the transepithelial movement of Der p 1 may have been facilitated by the inherent proteolytic activity of Der p 1.

Antagonism and/or inhibition of intestinal tight junction function has been demonstrated to slow, delay and/or reverse the progression toward diabetes. (see U.S. Pat. No. 7,026,294 and US Application Publication No. 20060287233). Thus, the compositions and methods of the present invention are believed to be useful to prevent and or delay the onset of diabetes, and to mitigate the long-term complications of diabetes. Further, the permeability changes associated with autoimmune diseases are long standing, and early intervention using the compositions and methods of the present invention is believed to have untold benefits to the diabetic patient.

Zonula occludens toxin (ZOT), which is produced by *Vibrio cholerae*, has been characterized by Fasano et al., (Proc. Natl. Acad. Sci., USA, 8:5242-5246 (1991)) and the sequence has been determined (GenBank accession no. A43864). ZOT increases the intestinal permeability of rabbit ileal mucosa by modulating the structure of intercellular tight junctions. Mammalian proteins that are immunologically and functionally related to ZOT have been identified. See U.S. Pat. No. 5,945,510. These proteins, referred to as "zonulin," function as the physiological effector of mammalian tight junctions. These proteins are useful for enhancing absorption of therapeutic agents across tight junctions of intestinal and nasal mucosa, as well as across tight junctions of the blood brain barrier.

ZOT and ΔG have been previously identified as tight junction agonists, i.e., compounds that mediate or facilitate or augment the physiological, transient opening of tight junctions that form a barrier between adjacent epithelial cells. The ability of ZOT and ΔG to open tight junctions has been used to facilitate the transfer of macromolecule across epithelial barriers (see U.S. Pat. No. 5,665,389 and Salama et al. *J. Pharmacology and Experimental Therapeutics* 312(1):199-205, 2005). ZOT has been shown to act as a tight junction agonist that allows opening of tight junctions between adjacent mucosal epithelial cells. Compounds that antagonize the opening of tight junctions have been identified (see U.S. Pat. Nos. 6,458,925, 6,670,448, 6,936,689 and 7,189,696). One such antagonist, AT-1001, is currently in Phase II clinical trials for the treatment of celiac disease where it protects against loss of gut mucosal barrier function.

Peptide antagonists of tight junction opening were described in U.S. Pat. No. 6,458,925 (corresponds to WO 00/07609), which is incorporated by reference herein in its entirety. Peptide antagonists of tight junction opening may bind to the receptor utilized by the zonula occludens toxin expressed by *Vibrio cholerae*, and not function to physiologically modulate the opening of mammalian tight junctions. The peptide antagonists may competitively inhibit the binding of ZOT and/or zonulin to the ZOT receptor, thereby inhibiting the ability of ZOT and/or zonulin to physiologically modulate the opening of mammalian tight junctions.

There remains a need in the art for compositions and methods to treat such diseases characterized by excessive or undesirable permeability of tissues containing tight junctions. This need and others are met by the present invention.

SUMMARY OF THE INVENTION

The present invention provides antagonists of tight junctions. Tight junction antagonists of the invention may be peptide tight junction antagonists. Peptide tight junction antagonists of the invention may be of any length. In some embodiments, peptide tight junction antagonists according to the invention may be three amino acids in length. In some embodiments, peptide tight junction antagonists according to the invention may be four amino acids in length. In some embodiments, peptide tight junction antagonists according to the invention may be five amino acids in length. In some embodiments, peptide tight junction antagonists according to the invention may be six amino acids in length. In some embodiments, peptide tight junction antagonists according to the invention may be seven amino acids in length. In some embodiments, a peptide tight junction antagonist of the invention may comprise, consist essentially of, or consist of a peptide that comprises, consists essentially of or consists of an amino acid sequence selected from the group consisting of SEQ ID NOs: 2-69. In some embodiments, a peptide tight junction antagonist of the invention may comprise, consist essentially of, or consist of a peptide that comprises, consists essentially of or consists of an amino acid sequence selected from the group consisting of SEQ ID NOs: 3-11, 13, 17, 18, 20-32, 34, 35, 54, 57, and 67-69.

The present invention also provides compositions, e.g., pharmaceutical compositions, comprising one or more peptide tight junction antagonists of the invention. Compositions of the invention may comprise one or more peptide tight junction antagonists. Peptide tight junction antagonists for use in compositions of the invention may be of any length. In some embodiments, such peptide antagonists of tight junctions are three amino acids in length. Suitable peptide tight junction antagonists for use in the compositions of the invention include, but are not limited to, peptide tight junction antagonists that comprise, consist essentially of, or consist of a peptide that comprises, consists essentially of; or consists of an amino acid sequence selected from the group consisting of SEQ ID NOs: 2-69. In some embodiments, peptide tight junction antagonists for use in the compositions of the invention include, but are not limited to, peptide tight junction antagonists that comprise, consist essentially of; or consist of a peptide that comprises, consists essentially of, or consists of an amino acid sequence selected from the group consisting of SEQ ID NOs: 3-11, 13, 17, 18, 20-32, 34, 35, 54, 57, and 67-69. Compositions of the invention may further comprise one or more additional therapeutic agents. Suitable additional therapeutic agents include, but are not limited to, aminosalicylates, corticosteroids, immunomodulators, antibiotics, cytokines, chemokines and biologic therapeutics. Compositions of the invention may comprise one or more pharmaceutically acceptable excipients, for example, buffers, buffer salts, bulking agents, salts, surface active agents, acids, bases, sugars, binders and the like.

Compositions of the invention may be formulated for any type of delivery. For example, compositions of the invention may be formulated for intestinal delivery, e.g., may be delayed release compositions. Compositions of the invention may be formulated for pulmonary delivery.

In some embodiments, the invention provides methods of treating an excessive or undesirable permeability of a tissue containing tight junctions comprising administering to a subject in need thereof a composition comprising a peptide tight junction antagonist of the invention as described above. As used herein, a "subject" may be any mammal, for example, a human, dog, cat, horse, cow, etc. In some embodiments, a subject may be a human. In other embodiments, a subject may be a dog.

Compositions for treating an excessive or undesirable permeability of a tissue containing tight junctions may comprise one or more peptide tight junction antagonists as described above. Peptide tight junction antagonists for use in compositions for treating an excessive or undesirable permeability of a tissue containing tight junctions may be of any length. In some embodiments, such peptide tight junction antagonists of are three amino acids in length.

Suitable peptide tight junction antagonists for use in compositions for treating an excessive or undesirable permeability of a tissue containing tight junctions include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating an excessive or undesirable permeability of a tissue containing tight junctions include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69. Compositions for treating an excessive or undesirable permeability of a tissue containing tight junctions may further comprise one or more additional therapeutic agents. Suitable additional therapeutic agents include, but are not limited to, aminosalicylates, corticosteroids, immunomodulators, antibiotics, cytokines, chemokines and biologic therapeutics. Compositions for use in treating an excessive or undesirable permeability of a tissue containing tight junctions may comprise one or more pharmaceutically acceptable excipients, for example, buffers, buffer salts, bulking agents, salts, surface active agents, acids, bases, sugars, binders and the like.

Compositions for treating an excessive or undesirable permeability of a tissue containing tight junctions may be formulated for any type of delivery. For example, compositions for treating an excessive or undesirable permeability of a tissue containing tight junctions may be formulated for intestinal delivery, e.g., may be delayed release compositions. Compositions for treating an excessive or undesirable permeability of a tissue containing tight junctions may be formulated for pulmonary delivery.

In some embodiments, the invention provides methods of treating Celiac disease comprising administering to a subject in need thereof a composition comprising a peptide tight junction antagonist of the invention as described above. Compositions for treating Celiac disease may comprise one or more peptide tight junction antagonists as described above. Peptide tight junction antagonists for use in compositions for treating Celiac disease may be of any length. In some embodiments, such peptide tight junction antagonists are three amino acids in length.

Suitable peptides for use in the compositions for treating Celiac disease include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating Celiac disease include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69. Compositions for use in treating Celiac disease may comprise one or more pharmaceutically acceptable excipients, for example, buffers, buffer salts, bulking agents, salts, surface active agents, acids, bases, sugars, binders and the like.

Compositions for treating Celiac disease may be formulated for any type of delivery. For example, such compositions may be formulated for intestinal delivery, e.g., may be delayed release compositions.

In some embodiments, the invention provides methods of treating inflammatory bowel disease comprising administering to a subject in need thereof a composition comprising a peptide tight junction antagonist as described above. Compositions for treating inflammatory bowel disease may comprise one or more peptide tight junction antagonists as described above. Peptide tight junction antagonists for use in compositions for treating inflammatory bowel disease may be of any length. In some embodiments, such peptide tight junction antagonists are three amino acids in length.

Suitable peptides for use in the compositions for treating inflammatory bowel disease include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating inflammatory bowel disease include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69.

Compositions for treating inflammatory bowel disease may further comprise one or more additional therapeutic agents. Suitable additional therapeutic agents include, but are not limited to, aminosalicylates, corticosteroids, immunomodulators, antibiotics, cytokines, chemokines and biologic therapeutics. Compositions for use in treating inflammatory bowel disease may comprise one or more pharmaceutically acceptable excipients, for example, buffers, buffer salts, bulking agents, salts, surface active agents, acids, bases, sugars, binders and the like.

Compositions for treating inflammatory bowel disease may be formulated for any type of delivery. For example, such compositions may be formulated for intestinal delivery, e.g., may be delayed release compositions.

The present invention provides methods and materials for treating Crohn's disease. In some embodiments, the invention provides methods of treating Crohn's disease comprising administering to a subject in need thereof a composition comprising a peptide tight junction antagonist as described above.

Compositions for treating Crohn's disease may comprise one or more peptide tight junction antagonists as described above. Peptide tight junction antagonists for use in compositions for treating Crohn's disease may be of any length. In some embodiments, such peptide tight junction antagonists are three amino acids in length.

Suitable peptides for use in the compositions for treating Crohn's disease include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating Crohn's disease include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69.

Compositions for treating Crohn's disease may further comprise one or more additional therapeutic agents. Suitable additional therapeutic agents include, but are not limited to, aminosalicylates, corticosteroids, immunomodulators, antibiotics, cytokines, chemokines and biologic therapeutics. Compositions for use in treating Crohn's disease may comprise one or more pharmaceutically acceptable excipients, for example, buffers, buffer salts, bulking agents, salts, surface active agents, acids, bases, sugars, binders and the like.

Compositions for treating Crohn's disease may be formulated for any type of delivery. For example, such compositions may be formulated for intestinal delivery, e.g., may be delayed release compositions.

The present invention provides methods and materials for treating ulcerative colitis. In some embodiments, the invention provides methods of treating ulcerative colitis comprising administering to a subject in need thereof a composition comprising a peptide tight junction antagonist as described above.

Compositions for treating ulcerative colitis may comprise one or more peptide tight junction antagonists as described above. Peptide tight junction antagonists for use in compositions for treating ulcerative colitis may be of any length. In some embodiments, such peptide tight junction antagonists are three amino acids in length.

Suitable peptides for use in the compositions for treating ulcerative colitis include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating ulcerative colitis include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69.

Compositions for treating ulcerative colitis may further comprise one or more therapeutic agents. Suitable therapeutic agents include, but are not limited to, aminosalicylates, corticosteroids, immunomodulators, antibiotics, cytokines, chemokines and biologic therapeutics. Compositions for use in treating ulcerative colitis may comprise one or more pharmaceutically acceptable excipients, for example, buffers, buffer salts, bulking agents, salts, surface active agents, acids, bases, sugars, binders and the like.

Compositions for treating ulcerative colitis may be formulated for any type of delivery. For example, such compositions may be formulated for intestinal delivery, e.g., may be delayed release compositions.

The present invention provides methods and materials for treating acute respiratory distress syndrome. In some embodiments, the invention provides methods of treating acute respiratory distress syndrome comprising administering to a subject in need thereof a composition comprising a peptide tight junction antagonist as described above.

Compositions for treating acute respiratory distress syndrome may comprise one or more peptide tight junction antagonists as described above. Peptide tight junction antagonists for use in compositions for treating acute respiratory distress syndrome may be of any length. In some embodiments, such peptide tight junction antagonists are three amino acids in length.

Suitable peptides for use in the compositions for treating acute respiratory distress syndrome include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating acute respiratory distress syndrome include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69.

Compositions for treating acute respiratory distress syndrome may further comprise one or more therapeutic agents. Suitable therapeutic agents include, but are not limited to, aminosalicylates, corticosteroids, immunomodulators, antibiotics, cytokines, chemokines and biologic therapeutics. Compositions for use in treating acute respiratory distress syndrome may comprise one or more pharmaceutically acceptable excipients, for example, buffers, buffer salts, bulking agents, salts, surface active agents, acids, bases, sugars, binders and the like.

Compositions for treating acute respiratory distress syndrome may be formulated for any type of delivery. For example, such compositions may be formulated for pulmonary delivery, e.g., may be solution aerosol or powder aerosol compositions.

The present invention provides methods and materials for treating acute lung injury. In some embodiments, the invention provides methods of treating acute lung injury comprising administering to a subject in need thereof a composition comprising a peptide tight junction antagonist as described above.

Compositions for treating acute lung injury may comprise one or more peptide tight junction antagonists as described above. Peptide tight junction antagonists for use in compositions for treating ac acute lung injury may be of any length. In some embodiments, such peptide tight junction antagonists are three amino acids in length.

Suitable peptides for use in the compositions for treating acute lung injury include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating acute lung injury include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69.

Compositions for treating acute lung injury may further comprise one or more therapeutic agents. Suitable therapeutic agents include, but are not limited to, aminosalicylates, corticosteroids, immunomodulators, antibiotics, cytokines, chemokines and biologic therapeutics. Compositions for use in treating acute lung injury may comprise one or more pharmaceutically acceptable excipients, for example, buffers, buffer salts, bulking agents, salts, surface active agents, acids, bases, sugars, binders and the like.

Compositions for treating acute lung injury may be formulated for any type of delivery. For example, such compositions may be formulated for pulmonary delivery, e.g., may be solution aerosol or powder aerosol compositions.

The present invention provides methods and materials for treating chronic obstructive pulmonary disorder. Chronic obstructive pulmonary disorder may be emphysema or bronchitis. In some embodiments, the invention provides methods of treating chronic obstructive pulmonary disorder comprising administering to a subject in need thereof a composition comprising a peptide tight junction antagonist as described above.

Compositions for treating chronic obstructive pulmonary disorder may comprise one or more peptide tight junction antagonists as described above. Peptide tight junction antagonists for use in compositions for treating ac chronic obstructive pulmonary disorder may be of any length. In some embodiments, such peptide tight junction antagonists are three amino acids in length.

Suitable peptides for use in the compositions for treating chronic obstructive pulmonary disorder include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating chronic obstructive pulmonary disorder include, but are not limited to, peptide tight junction antagonists that comprise, consist essentially of, or consist of a peptide that comprises, consists essentially of; or consists of an amino acid sequence selected from the group consisting of SEQ ID NOs: 3-11, 13, 17, 18, 20-32, 34, 35, 54, 57, and 67-69.

Compositions for treating chronic obstructive pulmonary disorder may further comprise one or more therapeutic agents. Suitable therapeutic agents include, but are not limited to, aminosalicylates, corticosteroids, immunomodulators, antibiotics, cytokines, chemokines and biologic therapeutics. Compositions for use in treating chronic obstructive pulmonary disorder may comprise one or more pharmaceutically acceptable excipients, for example, buffers, buffer salts, bulking agents, salts, surface active agents, acids, bases, sugars, binders and the like.

Compositions for treating chronic obstructive pulmonary disorder may be formulated for any type of delivery. For example, such compositions may be formulated for pulmonary delivery, e.g., may be solution aerosol or powder aerosol compositions.

The present invention provides methods and materials for treating asthma. In some embodiments, the invention provides methods of treating asthma comprising administering to a subject in need thereof a composition comprising a peptide tight junction antagonist as described above.

Compositions for treating asthma may comprise one or more peptide tight junction antagonists as described above. Peptide tight junction antagonists for use in compositions for treating ac asthma may be of any length. In some embodiments, such peptide tight junction antagonists are three amino acids in length.

Suitable peptides for use in the compositions for treating asthma include, but are not limited to, peptide tight junction antagonists that comprise, consist essentially of, or consist of a peptide that comprises, consists essentially of; or consists of an amino acid sequence selected from the group consisting of SEQ ID NOs: 2-69. In some embodiments, peptide tight junction antagonists for use in compositions for treating asthma include, but are not limited to, peptide tight junction antagonists that comprise, consist essentially of; or consist of a peptide that comprises, consists essentially of, or consists of an amino acid sequence selected from the group consisting of SEQ ID NOs: 3-11, 13, 17, 18, 20-32, 34, 35, 54, 57, and 67-69.

Compositions for treating asthma may further comprise one or more therapeutic agents. Suitable therapeutic agents include, but are not limited to, bronchodilators, anti-inflammatories, aminosalicylates, corticosteroids, immunomodulators, antibiotics, cytokines, chemokines and biologic therapeutics. Compositions for use in treating asthma may comprise one or more pharmaceutically acceptable excipients, for example, buffers, buffer salts, bulking agents, salts, surface active agents, acids, bases, sugars, binders and the like.

Compositions for treating asthma may be formulated for any type of delivery. For example, such compositions may be formulated for pulmonary delivery, e.g., may be solution aerosol or powder aerosol compositions.

The present invention provides methods and materials for treating type 1 diabetes. In some embodiments, the invention provides methods of treating type 1 diabetes comprising administering to a subject in need thereof a composition comprising a peptide tight junction antagonist as described above.

Compositions for treating type 1 diabetes may comprise one or more peptide tight junction antagonists as described above. Peptide tight junction antagonists for use in compositions for treating ac type 1 diabetes may be of any length. In some embodiments, such peptide tight junction antagonists are three amino acids in length.

Suitable peptides for use in the compositions for treating type 1 diabetes include, but are not limited to, peptide tight junction antagonists that comprise, consist essentially of, or consist of a peptide that comprises, consists essentially of, or consists of an amino acid sequence selected from the group consisting of SEQ ID NOs: 2-69. In some embodiments, peptide tight junction antagonists for use in compositions for treating type 1 diabetes include, but are not limited to, peptide tight junction antagonists that comprise, consist essentially of, or consist of a peptide that comprises, consists essentially of, or consists of an amino acid sequence selected from the group consisting of SEQ ID NOs: 3-11, 13, 17, 18, 20-32, 34, 35, 54, 57, and 67-69.

Compositions for treating type 1 diabetes may further comprise one or more therapeutic agents. Suitable therapeutic agents include, but are not limited to, insulin, insulin mimetics, immunomodulators, antibiotics, cytokines, chemokines and biologic therapeutics. Compositions for use in treating type 1 diabetes may comprise one or more pharmaceutically acceptable excipients, for example, buffers, buffer salts, bulking agents, salts, surface active agents, acids, bases, sugars, binders and the like.

Compositions for treating type 1 diabetes may be formulated for any type of delivery. For example, such compositions may be formulated for intestinal delivery, e.g., may be delayed release compositions.

DETAILED DESCRIPTION OF THE INVENTION

Figure 1:
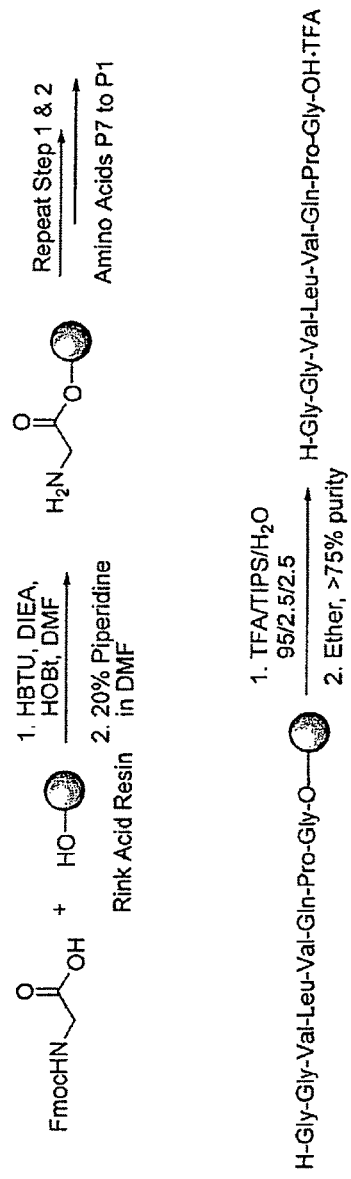
FIG. 1 is a schematic showing the steps involved in solid phase synthesis of an exemplary tight junction antagonist of the invention.
Figure 2:
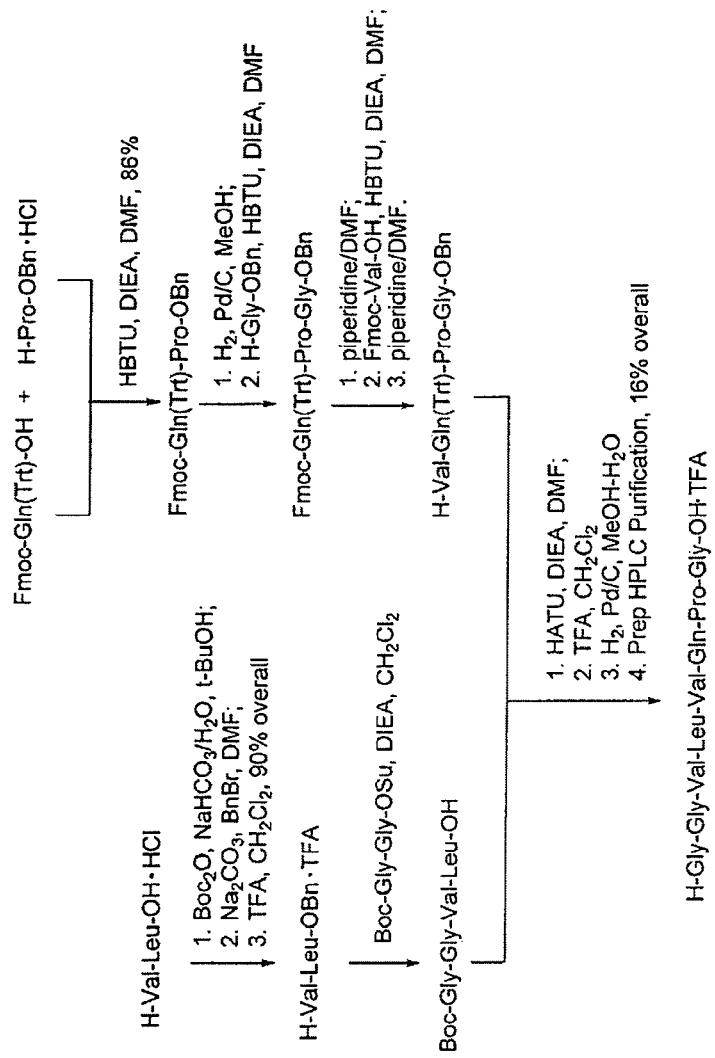
FIG. 2 is a schematic showing the steps involved in solution phase synthesis of an exemplary tight junction antagonist of the invention.

As used herein, "about" used to modify a numerical value means within 10% of the value.

Antagonists of Tight Junction Opening

As used herein, tight junction antagonists prevent, inhibit or reduce the opening of tight junctions, for example, the opening of tight junctions induced by a tight junction agonist. A tight junction antagonist may bind to a receptor that mediates tight junction agonist induced opening of tight junctions. For example, a tight junction antagonist may bind to the ZOT receptor and prevent, inhibit, reduce or reverse the tight junction opening triggered by the tight junction agonist ZOT.

As used herein a subject is any animal, e.g., mammal, upon which methods of the invention may be practiced and/or to which materials of the present invention may be administered. Subjects include, but are not limited to, humans.

Antagonists of the invention may comprise peptide antagonists. An example of a peptide tight junction antagonist is a peptide that consists of the amino acid sequence Gly Gly Val Leu Val Gln Pro Gly (SEQ ID NO:1). Further examples of peptide tight junction antagonists are peptides that consist of the amino acid sequences Gly Val Leu Val Gln Pro Gly (SEQ ID NO:2), Val Leu Val Gln Pro Gly (SEQ ID NO:3), Leu Val Gln Pro Gly (SEQ ID NO:4), Val Gln Pro Gly (SEQ ID NO:5), or Gln Pro Gly (SEQ ID NO:6). Additional examples of peptide tight junction antagonists of the invention include, but are not limited to, peptides wherein one or more amino acids of the amino acid sequences Gly Val Leu Val Gln Pro Gly (SEQ ID NO:2), Val Leu Val Gln Pro Gly (SEQ ID NO:3), Leu Val Gln Pro Gly (SEQ ID NO:4), Val Gln Pro Gly (SEQ ID NO:5), or Gln Pro Gly (SEQ ID NO:6) have been substituted with a different amino acid. In some embodiments, only one position will be substituted. In some embodiments, two positions will be substituted. Substitutions may be made at any position of SEQ ID NO:1.

The peptide tight junction antagonists can be chemically synthesized and purified using well-known techniques, such as described in *High Performance Liquid Chromatography of Peptides and Proteins: Separation Analysis and Conformation*, Eds. Mant et al., C.R.C. Press (1991), and a peptide synthesizer, such as Symphony (Protein Technologies, Inc); or by using recombinant DNA techniques, i.e., where the nucleotide sequence encoding the peptide is inserted in an appropriate expression vector, e.g., an *E. coli* or yeast expression vector, expressed in the respective host cell, and purified therefrom using well-known techniques.

Compositions

Typically, compositions, such as pharmaceutical compositions, comprising a tight junction antagonist (e.g., peptide tight junction antagonist) comprise a pharmaceutically effective amount of that antagonist. The pharmaceutically effective amount of tight junction antagonist (e.g., peptide tight junction antagonist) employed in any given composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. Generally, the amount of tight junction antagonist used for preventing, ameliorating and/or treating a disease in a subject will be in the range of about 1 µg to 1 g, preferably from about 1 mg to about 1000 mg, or from about 10 mg to about 100 mg, or from about 10 mg to about 50 mg, or from about 10 mg to about 25 mg of antagonist.

Compositions of the invention may comprise one or more peptide tight junction antagonists at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 6 wt %, from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1 wt % to about 0.7 wt %, from about 0.1 wt % to about 0.6 wt %, from about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition. Compositions of the invention may comprise one or more peptide tight junction antagonists at a level of about 0.1 wt %, about 0.2 wt %, about 0.3 wt %, about 0.4 wt %, about 0.5 wt %, about 0.6 wt %, about 0.7 wt %, about 0.8 wt %, or about 0.9 wt % based on the total weight of the composition.

Compositions of the invention may comprise one or more peptide tight junction antagonists at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 6 wt %, from about 1 wt % to about 5 wt %, from about 1 wt % to about 4 wt %, from about 1 wt % to about 3 wt %, or from about 1 wt % to about 2 wt % of the total weight of the composition. Compositions of the invention may comprise one or more peptide tight junction antagonists at a level of about 1 wt %, about 2 wt %, about 3 wt %, about 4 wt %, about 5 wt %, about 6 wt %, about 7 wt %, about 8 wt %, or about 9 wt % based on the total weight of the composition.

Compositions of the invention may formulated for pulmonary delivery (e.g., may be pulmonary dosage forms). Typically such compositions may be provided as pharmaceutical aerosols, e.g., solution aerosols or powder aerosols. Those of skill in the art are aware of many different methods and devices for the formation of pharmaceutical aerosols, for example, those disclosed by Sciarra and Sciarra, Aerosols, in *Remington: The Science and Practice of Pharmacy*, 20th Ed., Chapter 50, Gennaro et al. Eds., Lippincott, Williams and Wilkins Publishing Co., (2000).

In one embodiment, the dosage forms are in the form of a powder aerosol (i.e., comprise particles). These are particularly suitable for use in inhalation delivery systems. Powders may comprise particles of any size suitable for administration to the lung.

Powder formulations may optionally contain at least one particulate pharmaceutically acceptable carrier known to those of skill in the art. Examples of suitable pharmaceutical carriers include, but are not limited to, saccharides, including monosaccharides, disaccharides, polysaccharides and sugar alcohols such as arabinose, glucose, fructose, ribose, mannose, sucrose, trehalose, lactose, maltose, starches, dextran, mannitol or sorbitol. In one embodiment, a powder formulation may comprise lactose as a carrier.

Powder formulations may be contained in any container known to those in the art. Containers may be capsules of, for example, gelatin or plastic, or in blisters (e.g. of aluminum or plastic), for use in a dry powder inhalation device. In some embodiments, the total weight of the formulation in the container may be from about 5 mg to about 50 mg. In other embodiments, powder formulations may be contained in a reservoir in a multi-dose dry powder inhalation device adapted to deliver a suitable amount per actuation.

Powder formulations typically comprise small particles. Suitable particles can be prepared using any means known in the art, for example, by grinding in an airjet mill, ball mill or vibrator mill, sieving, microprecipitation, spray-drying, lyophilisation or controlled crystallisation. Typically, particles will be about 10 microns or less in diameter. Particles for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. In some embodiments, particles for use in the invention may be about 1 micron, about 2 microns, about 3 microns, about 4 microns, about 5 microns, about 6 microns, about 7 microns, about 8 microns, about 9 microns, or about 10 microns in diameter.

In one embodiment, the dosage forms are in the form of a solution aerosol (i.e., comprise droplets). Typically, droplets will be about 10 microns or less in diameter. Droplets for use in the compositions of the invention may have a diameter of from about 0.1 microns to about 10 microns, from about 0.1 microns to about 9 microns, from about 0.1 microns to about 8 microns, from about 0.1 microns to about 7 microns, from about 0.1 microns to about 6 microns, from about 0.1 microns to about 5 microns, from about 0.1 microns to about 4 microns, from about 0.1 microns to about 3 microns, from about 0.1 microns to about 2 microns, from about 0.1 microns to about 1 micron, from about 0.1 microns to about 0.5 microns, from about 1 micron to about 10 microns, from about 1 micron to about 9 microns, from about 1 micron to about 8 microns, from about 1 micron to about 7 microns, from about 1 micron to about 6 microns, from about 1 micron to about 5 microns, from about 1 micron to about 4 microns, from about 1 micron to about 3 microns, from about 1 micron to about 2 microns, from about 2 microns to about 10 microns, from about 2 microns to about 9 microns, from about 2 microns to about 8 microns, from about 2 microns to about 7 microns, from about 2 microns to about 6 microns, from about 2 microns to about 5 microns, from about 2 microns to about 4 microns, or from about 2 microns to about 3 microns. In some embodiments, particles and/or droplets for use in the invention may be about 1 micron, about 2 microns, about 3 microns, about 4 microns, about 5 microns, about 6 microns, about 7 microns, about 8 microns, about 9 microns, or about 10 microns in diameter.

The compositions of the invention may be formulated for enteric delivery, for example, may comprise one or more coatings that may include, for example, a delayed-release coating containing one or more enteric agents. A delayed-release coating is typically substantially stable in gastric fluid and substantially unstable (e.g., dissolves rapidly or is physically unstable) in intestinal fluid, thus providing for substantial release of the peptide tight junction antagonist from the composition in the duodenum or the jejunum.

The terms "stable in gastric fluid" or "stable in acidic environments" refers to a composition that releases 30% or less by weight of the total peptide tight junction antagonist in the composition in gastric fluid with a pH of 5 or less, or simulated gastric fluid with a pH of 5 or less, in approximately sixty minutes. Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

Compositions of the of the invention may release from about 0% to about 30%, from about 0% to about 25%, from about 0% to about 20%, from about 0% to about 15%, from about 0% to about 10%, from about 0% to about 5%, from about 5% to about 30%, from about 5% to about 25%, from about 5% to about 20%, from about 5% to about 15%, or from about 5% to about 10% by weight of the total peptide tight junction antagonist in the composition in gastric fluid with a pH of 5 or less or simulated gastric fluid with a pH of 5 or less, in approximately sixty minutes. Compositions of the invention may release about 1%, about 2%, about 3%, about 4%, about 5%, about 6%, about 7%, about 8%, about 9%, or about 10% by weight of the total peptide tight junction antagonist in the composition in gastric fluid with a pH of 5 or less, or simulated gastric fluid with a pH of 5 or less, in approximately sixty minutes.

The term "unstable in intestinal fluid" refers to a composition that releases 70% or more by weight of the total peptide tight junction antagonist in the composition in intestinal fluid or simulated intestinal fluid in approximately sixty minutes. The term "unstable in near neutral to alkaline environments" refers to a composition that releases 70% or more by weight of the total amount of tight junction antagonist in the composition in intestinal fluid with a pH of 5 or greater, or simulated intestinal fluid with a pH of 5 or greater, in approximately ninety minutes. For example, a composition that is unstable in near neutral or alkaline environments may release 70% or more by weight of the total peptide tight junction antagonist in the composition in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 60 minutes, or from about 30 minutes to about 60 minutes.

In addition to one or more peptide tight junction antagonists, compositions of the invention may further comprise one or more additional therapeutic agents. Additional therapeutic agents include, but are not limited to, steroids and other anti-inflammatory compounds. Suitable additional therapeutic agents may include one or more of aminosalicylates, corticosteroids, immunomodulators, antibiotics, cytokines, chemokines and biologic therapies. Examples of suitable therapeutic agents that may be included in the compositions of the invention to treat IBD (e.g., Crohn's disease and/or ulcerative colitis) include, but are not limited to:

5-ASA agents (e.g., Sulfasalazine), Azulfidine®, Asacol,® Dipentum,® Pentasa,® and Rowasa®;

Antibiotics, for example, metronidazole (Flagyl®) and ciprofloxacin (Cipro®), although there are many others that may be effective in certain individuals;

Steroids, e.g., corticosteroids. Suitable steroids include, but are not limited to, prednisone, hydrocortisone, Medrol®, and budesonide multiple-release capsule MRC (EntocortREC®).

6-mercaptopurine (6-MP, Purinethol®) and azathioprine (Imuran®); and antibodies against inflammatory cytokines, e.g., Infliximab (Remicade™)

Compositions of the invention may also comprise one or more pharmaceutically acceptable excipients. Suitable excipients include, but are not limited to, buffers, buffer salts, bulking agents, salts, surface active agents, acids, bases, sugars, binders, and the like.

Methods of Use

The compositions of the invention can be used for preventing, slowing the onset of, ameliorating and/or treating any disease associated with an excessive or undesirable permeability of tissues containing tight junctions. Specific examples of diseases of this type include, but are not limited to, Celiac Disease, Inflammatory Bowel Disease, Crohn's disease, ulcerative colitis, Irritable Bowel Syndrome, Type 1 Diabetes, Asthma, Acute Respiratory Distress Syndrome, Acute Lung Injury, and Chronic Obstructive Pulmonary Disease. In one embodiment, the present invention provides a method of treating Celiac disease comprising administering to a subject in need thereof a composition comprising a peptide tight junction antagonist. In one embodiment, the present invention provides a method of treating Crohn's disease comprising administering to a subject in need thereof a composition comprising a peptide tight junction antagonist. In one embodiment, the present invention provides a method of treating ulcerative colitis comprising administering to a subject in need thereof a composition comprising a peptide tight junction antagonist. In one embodiment, the present invention provides a method of treating irritable bowel syndrome comprising administering to a subject in need thereof a composition comprising a peptide tight junction antagonist. In one embodiment, the present invention provides a method of treating type 1 diabetes comprising administering to a subject in need thereof a composition comprising a peptide tight junction antagonist. In one embodiment, the present invention provides a method of treating asthma comprising administering to a subject in need thereof a composition comprising a peptide tight junction antagonist. In one embodiment, the present invention provides a method of treating acute respiratory distress syndrome comprising administering to a subject in need thereof a composition comprising a peptide tight junction antagonist. In one embodiment, the present invention provides a method of treating acute lung injury comprising administering to a subject in need thereof a composition comprising a peptide tight junction antagonist. In one embodiment, the present invention provides a method of treating chronic obstructive pulmonary disease comprising administering to a subject in need thereof a composition comprising a peptide tight junction antagonist.

In some embodiments, compositions of the invention may be administered repeatedly over a protracted period, i.e., may be chronically administered. Typically, compositions may be administered one or more times each day in an amount suitable to prevent an attack of, reduce the likelihood of an attack of, or reduce the severity of an attack of the underlying disease condition (e.g., Celiac disease, IBD etc.). Such compositions may be administered chronically, for example, one or more times daily over a plurality of days.

In some embodiments, compositions of the invention may be used to treat acute attacks of the underlying disease (e.g., Celiac disease, IBD (e.g., Crohn's disease and/or ulcerative colitis)). Typically, embodiments of this type will require administration of the compositions of the invention to a subject undergoing an attack in an amount suitable to reduce the severity of the attack. One or more administrations may be used.

The following examples are provided for illustrative purposes only, and are in no way intended to limit the scope of the present invention.

EXAMPLES

Example 1

Measurement of the Inhibition of the Decrease in Trans Epithelial Electric Resistance (TEER) and Epithelial Flux of a Fluorescent Marker Lucifer Yellow CaCo2 cells form monolayers that exhibit tight junctions between adjacent cells. Treatment of CaCo2 monolayers with peptide FCIGRL (SEQ ID NO: 70) enhanced 51-fold Lucifer Yellow permeability through CaCo2 monolayers compared to vehicle alone. Peptide FCIGRL decreased TEER 16-fold in CaCo2 monolayers compared to vehicle alone. Antagonists of tight junctions can be identified by their ability to prevent or decrease the enhancement of the flux of compounds (e.g. Lucifer Yellow) through the monolayer induced by agonists of tight junctions (e.g., SEQ ID NO: 70). Antagonists of tight junctions can also be identified by their ability to prevent the decrease in TEER induced by agonists of tight junctions (e.g., SEQ ID NO: 70).

Tight junction antagonists can be identified using the following method:

Prepare Modified Hank's Balanced Salt Solution (MHBSS) by obtaining IL bottle of HBSS removing 10 ml of HBSS and replacing it with 10 ml HEPES buffer pH 7.0. Adjust pH to 7.4±0.1 using concentrated NaOH (10N).

Remove Caco-2 cells from incubator, grown on 12-well, 3.0 μM, polycarbonate Transwell® filters (Corning) and record passage number, date cells seeded and age in days.

Aspirate cell culture medium from both the apical (AP) and basolateral (BL) compartments, replacing with 0.5 ml and 1.5 ml of MHBSS, respectively. Incubate cells at 37° C. for 30 minutes.

Using the MilliCell®-ERS instrument (Millipore), measure and record the transepithelial electrical resistance (TEER) across each filter and record.

Prepare a stock solution of the Antagonist Pretreatment Solution by dissolving the appropriate amount of antagonist in MHBSS. Vortex or sonicate the solution until it is clear then adjust pH to 7.4±0.1 using 1N NaOH. Preincubate each filter for 30 min with these solutions at 37° C. and 50 RPM.

Prepare stock solutions of Antagonist Treatment Solution by dissolving appropriate amounts of antagonist and agonist (for example, a peptide agonist such as a peptide having the sequence FCIGRL (SEQ ID NO: 70)) in 7.5 mM Lucifer Yellow solution in MHBSS. Vortex or sonicate the solution until it is clear then adjust pH to 7.4±0.1 using 1N NaOH.

Aspirate Antagonist Pretreatment Solution from the apical compartment of each filter (n=3 per condition) and replace with 0.5 ml of control and test solutions.

Place all plates into incubator set at 37° C. (±0.2), 50 RPM (±5) for a total of 180 minutes.

At t=30, 60, 120 and 180 minutes, measure and record the transepithelial electrical resistance (TEER) across each filter using the MilliCell-ERS instrument.

At t=60, 120 and 180 minutes remove 100 µl from each basolateral compartment and place it in a 96-well plate for Lucifer Yellow analysis, replace with 100 µl of HBSS.

Make a Lucifer Yellow standard curve with the following dilutions (7500 µM, 3750 µM, 750 µM, 375 µM, 75 µM, 37.5 µM, 7.5 µM, 3.75 µM, 0.75 µM) and pipette 100 µL of each into a 96-well plate except for the first three standards mentioned above which require a 1:10 dilution prior to transferring to the 96-well plate.

At t=0 make 1:10 dilutions of each starting Antagonist Treatment Solution mentioned above and pipette 100 µL of each into a 96-well plate.

At t=180 make 1:10 dilutions of Antagonist Treatment Solution from the apical compartment of each filter and pipette 100 µL of each into the 96-well plate.

Harvest the remaining start solutions and what is left in each apical compartment into 1.5 ml vials. Freeze at −20° C. for future analysis.

Analyze each 96-well plate in a Tecan Spectra Fluor Plus using Magellan at 485 and 535 nm.

Materials:

Cells: Caco-2 cells passage 40-60 grown on Transwell® plates for 21-28 days

Culture Medium: DMEM supplemented with 10% fetal bovine serum, 1% NEAA, 1% Penn/Strep Buffers: Hank's Balanced Salt Solution (HBSS) without calcium and magnesium Flasks: 100×20 mm Tissue culture dish Falcon.

Plates: 12 well polycarbonate Transwell® filters; 0.3 uM pore size

The results of these assays are provided in the following table. The first column of the table provides SEQ ID NO: of the peptide, the second column provides the sequence of the peptides tested, the third column provides the results of an assay of inhibition of the increase in Lucifer Yellow permeability induced by SEQ ID NO:70, and the fourth column provides the results of an assay of the inhibition of the reduction in TEER induced by SEQ ID NO: 70. SEQ ID NO: 70 is a 6-mer peptide tight junction agonist having the sequence FCIGRL. See US patent publication US 2005/0059593 A1. In the following tables + indicates attenuation of the effects of the tight junction agonist were observed and − indicates no attenuation of the effects of the tight junction agonist were observed.

TABLE 1

Tight junction antagonism by SEQ ID NOs:1-69

| SEQ ID NO: | Sequence | Reduced LY Permeability | Prevented TEER Reduction |
|---|---|---|---|
| 1 | Gly-Gly-Val-Leu-Val-Gln-Pro-Gly | + | + |
| 2 | Gly-Val-Leu-Val-Gln-Pro-Gly | − | − |
| 3 | Val-Leu-Val-Gln-Pro-Gly | + | + |
| 4 | Leu-Val-Gln-Pro-Gly | + | + |
| 5 | Val-Gln-Pro-Gly | + | + |
| 6 | Gln-Pro-Gly | + | + |
| 7 | Ala-Pro-Gly | + | + |
| 8 | Gln-Ala-Gly | + | + |
| 9 | Gln-Pro-Ala | + | + |
| 10 | (d)Gln-Pro-Gly | + | + |
| 11 | Gln-(d)Pro-Gly | + | + |
| 12 | (d)Gln-(d)Pro-Gly | − | − |
| 13 | Gly-Pro-Gln | + | + |
| 14 | Gly-(d)Pro-Gln | − | − |
| 15 | Gly-Pro-(d)Gln | − | − |
| 16 | Gly-(d)Pro-(d)Gln | − | − |
| 17 | Ala-Pro-Gly | + | + |
| 18 | His-Pro-Gly | + | + |
| 19 | Asp-Pro-Gly | − | − |
| 20 | Arg-Pro-Gly | + | + |
| 21 | Phe-Pro-Gly | + | + |
| 22 | Gly-Pro-Gly | + | + |

TABLE 1-continued

Tight junction antagonism by SEQ ID NOs:1-69

| SEQ ID NO: | Sequence | Reduced LY Permeability | Prevented TEER Reduction |
|---|---|---|---|
| 23 | Glu-Pro-Gly | + | + |
| 24 | Lys-Pro-Gly | + | + |
| 25 | Leu-Pro-Gly | + | + |
| 26 | Met-Pro-Gly | + | + |
| 27 | Asn-Pro-Gly | + | + |
| 28 | Ser-Pro-Gly | + | + |
| 29 | Tyr-Pro-Gly | + | + |
| 30 | Thr-Pro-Gly | + | − |
| 31 | Ile-Pro-Gly | + | + |
| 32 | Trp-Pro-Gly | + | + |
| 33 | Pro-Pro-Gly | − | − |
| 34 | Val-Pro-Gly | + | − |
| 35 | Glp-Pro-Gly | + | + |
| 36 | Glp-Val-Gly | − | − |
| 37 | Glp-Gln-Gly | − | − |
| 38 | Glp-Ser-Gly | − | − |
| 39 | Glp-Lys-Gly | − | − |
| 40 | Glp-Phe-Gly | − | − |
| 41 | Glp-Glu-Gly | − | − |
| 42 | Glp-Thr-Gly | − | − |
| 43 | Glp-Ile-Gly | − | − |
| 44 | Glp-Tyr-Gly | − | − |
| 45 | Glp-His-Gly | − | − |
| 46 | Glp-Asn-Gly | − | − |
| 47 | Glp-Arg-Gly | − | − |
| 48 | Glp-Gly-Gly | − | − |
| 49 | Glp-Trp-Gly | − | − |
| 50 | Glp-Asp-Gly | − | − |
| 51 | Glp-Met-Gly | − | − |
| 52 | Glp-Leu-Gly | − | − |
| 53 | Glp-Pro-Gln | − | − |
| 54 | Glp-Pro-Asn | − | + |
| 55 | Glp-Pro-Gln | − | − |
| 56 | Glp-Pro-Ser | − | − |
| 57 | Glp-Pro-Pro | − | + |
| 58 | Glp-Pro-Trp | − | − |
| 59 | Glp-Pro-Asp | − | − |
| 60 | Glp-Pro-His | − | − |

TABLE 1-continued

Tight junction antagonism by SEQ ID NOs:1-69

| SEQ ID NO: | Sequence | Reduced LY Permeability | Prevented TEER Reduction |
|---|---|---|---|
| 61 | Glp-Pro-Leu | − | − |
| 62 | Glp-Pro-Arg | − | − |
| 63 | Glp-Pro-Val | − | − |
| 64 | Glp-Pro-Lys | − | − |
| 65 | Glp-Pro-Glu | − | − |
| 66 | Glp-Pro-Phe | − | − |
| 67 | Gip-Pro-Ile | − | + |
| 68 | Glp-Pro-Met | − | + |
| 69 | Glp-Pro-Tyr | − | + |

Glp-Pyroglutamic acid

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method of treating an excessive or undesirable permeability of a tissue containing tight junctions in a subject comprising:
    administering to the subject a pharmaceutical composition comprising a peptide tight junction antagonist having three to five amino acids, and wherein the peptide is defined by the formula: X1-X2-X3-X4-X5; wherein:
    X1 is optional, and where present is a natural or non-natural amino acid,
    X2 is optional, and where present is a natural or non-natural amino acid,
    X3 is a natural or non-natural amino acid,
    X4 is selected from Pro and Ala, and
    X5 is Gly, Gln, or Ala.

2. The method of claim 1, wherein the subject has inflammatory bowel disease.

3. The method of claim 1, wherein the subject has Crohn's disease.

4. The method of claim 1, wherein the subject has ulcerative colitis.

5. The method of claim 1, wherein the subject has Celiac Disease.

6. The method of claim 1, wherein the subject has acute respiratory distress syndrome.

7. The method of claim 1, wherein the subject has acute lung injury.

8. The method of claim 1, wherein the subject has chronic obstructive pulmonary disorder.

9. The method of claim 1, wherein the subject has asthma.

10. The method of claim 1, wherein the subject has type I diabetes.

11. The method of claim 1, wherein the pharmaceutical composition is a solution or powder aerosol for pulmonary delivery.

12. The method of claim 1, wherein the pharmaceutical composition is formulated for enteric delivery.

13. The method of claim 1, wherein the pharmaceutical composition is administered one or more times per day for a plurality of days.

14. The method of claim 1, wherein the peptide has the amino acid sequence of SEQ ID NO: 4, 5, 6, 7, 8, 9, 10, 11, 13, 17, 18, 20, 21, 22, 23, 24, 25, 26, 27, 28, 29, 30, 31, 32, 34, or 35.

* * * * *

```
                    SEQUENCE LISTING

<160> NUMBER OF SEQ ID NOS: 70

<210> SEQ ID NO 1
<211> LENGTH: 8
<212> TYPE: PRT
<213> ORGANISM: Artificial Sequence
<220> FEATURE:
<223> OTHER INFORMATION: Tight junction antagonist

<400> SEQUENCE: 1

Gly Gly Val Leu Val Gln Pro Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Tight junction antagonist

<400> SEQUENCE: 2

Gly Val Leu Val Gln Pro Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Tight junction antagonist

<400> SEQUENCE: 3

Val Leu Val Gln Pro Gly
1               5

<210> SEQ ID NO 4
<211> LENGTH: 5
```

```
<212> TYPE: PRT
<213> ORGANISM: Artificial Sequence
<220> FEATURE:
<223> OTHER INFORMATION: Tight junction antagonist

<400> SEQUENCE: 4

Leu Val Gln Pro Gly
1               5

<210> SEQ ID NO 5
<211> LENGTH: 4
<212> TYPE: PRT
<213> ORGANISM: Artificial Sequence
<220> FEATURE:
<223> OTHER INFORMATION: Tight junction antagonist

<400> SEQUENCE: 5

Val Gln Pro Gly
1

<210> SEQ ID NO 6
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 6

Gln Pro Gly
1

<210> SEQ ID NO 7
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 7

Ala Pro Gly
1

<210> SEQ ID NO 8
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 8

Gln Ala Gly
1

<210> SEQ ID NO 9
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 9

Gln Pro Ala
1

<210> SEQ ID NO 10
<211> LENGTH: 3
<212> TYPE: PRT
```

```
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Gln may be D-Gln

<400> SEQUENCE: 10

Gln Pro Gly
1

<210> SEQ ID NO 11
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (2)..(2)
<223> OTHER INFORMATION: Pro may be D-Pro

<400> SEQUENCE: 11

Gln Pro Gly
1

<210> SEQ ID NO 12
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Gln may be D-Gln
<220> FEATURE:
<221> NAME/KEY: misc_feature
<222> LOCATION: (2)..(2)
<223> OTHER INFORMATION: Pro may be D-Pro

<400> SEQUENCE: 12

Gln Pro Gly
1

<210> SEQ ID NO 13
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 13

Gly Pro Gln
1

<210> SEQ ID NO 14
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (2)..(2)
<223> OTHER INFORMATION: Pro may be D-Pro

<400> SEQUENCE: 14

Gly Pro Gln
```

```
<210> SEQ ID NO 15
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (3)..(3)
<223> OTHER INFORMATION: Gln may be D-Gln

<400> SEQUENCE: 15

Gly Pro Gln
1

<210> SEQ ID NO 16
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (2)..(2)
<223> OTHER INFORMATION: Pro may be D-Pro
<220> FEATURE:
<221> NAME/KEY: misc_feature
<222> LOCATION: (3)..(3)
<223> OTHER INFORMATION: Gln may be D-Gln

<400> SEQUENCE: 16

Gly Pro Gln
1

<210> SEQ ID NO 17
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 17

Ala Pro Gly
1

<210> SEQ ID NO 18
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 18

His Pro Gly
1

<210> SEQ ID NO 19
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 19

Asp Pro Gly
1
```

```
<210> SEQ ID NO 20
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 20

Arg Pro Gly
1

<210> SEQ ID NO 21
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 21

Phe Pro Gly
1

<210> SEQ ID NO 22
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 22

Gly Pro Gly
1

<210> SEQ ID NO 23
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 23

Glu Pro Gly
1

<210> SEQ ID NO 24
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 24

Lys Pro Gly
1

<210> SEQ ID NO 25
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 25

Leu Pro Gly
1
```

```
<210> SEQ ID NO 26
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 26

Met Pro Gly
1

<210> SEQ ID NO 27
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 27

Asn Pro Gly
1

<210> SEQ ID NO 28
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 28

Ser Pro Gly
1

<210> SEQ ID NO 29
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 29

Tyr Pro Gly
1

<210> SEQ ID NO 30
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 30

Thr Pro Gly
1

<210> SEQ ID NO 31
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 31

Ile Pro Gly
1

<210> SEQ ID NO 32
```

```
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 32

Trp Pro Gly
1

<210> SEQ ID NO 33
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 33

Pro Pro Gly
1

<210> SEQ ID NO 34
<211> LENGTH: 3
<212> TYPE: PRT
<213> ORGANISM: Artificial Sequence
<220> FEATURE:
<223> OTHER INFORMATION: Tight junction antagonist

<400> SEQUENCE: 34

Val Pro Gly
1

<210> SEQ ID NO 35
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 35

Xaa Pro Gly
1

<210> SEQ ID NO 36
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 36

Xaa Val Gly
1

<210> SEQ ID NO 37
<211> LENGTH: 3
<212> TYPE: PRT
<213> ORGANISM: Artificial Sequence
<220> FEATURE:
<223> OTHER INFORMATION: Tight junction antagonist
<220> FEATURE:
```

```
<221> NAME/KEY: misc_feature
<222> LOCATION: (1)..(1)
<223> OTHER INFORMATION: Xaa may be pyroglutamic acid

<400> SEQUENCE: 37

Xaa Gln Gly
1

<210> SEQ ID NO 38
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 38

Xaa Ser Gly
1

<210> SEQ ID NO 39
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 39

Xaa Lys Gly
1

<210> SEQ ID NO 40
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 40

Xaa Phe Gly
1

<210> SEQ ID NO 41
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 41

Xaa Glu Gly
1

<210> SEQ ID NO 42
```

```
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 42

Xaa Thr Gly
1

<210> SEQ ID NO 43
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 43

Xaa Ile Gly
1

<210> SEQ ID NO 44
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 44

Xaa Tyr Gly
1

<210> SEQ ID NO 45
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 45

Xaa His Gly
1

<210> SEQ ID NO 46
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 46
```

```
Xaa Asn Gly
1

<210> SEQ ID NO 47
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 47

Xaa Arg Gly
1

<210> SEQ ID NO 48
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 48

Xaa Gly Gly
1

<210> SEQ ID NO 49
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 49

Xaa Trp Gly
1

<210> SEQ ID NO 50
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 50

Xaa Asp Gly
1

<210> SEQ ID NO 51
<211> LENGTH: 3
<212> TYPE: PRT
<213> ORGANISM: Artificial Sequence
<220> FEATURE:
<223> OTHER INFORMATION: Tight junction antagonist
```

```
<220> FEATURE:
<221> NAME/KEY: misc_feature
<222> LOCATION: (1)..(1)
<223> OTHER INFORMATION: Xaa may be pyroglutamic acid

<400> SEQUENCE: 51

Xaa Met Gly
1

<210> SEQ ID NO 52
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 52

Xaa Leu Gly
1

<210> SEQ ID NO 53
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 53

Xaa Pro Gln
1

<210> SEQ ID NO 54
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 54

Xaa Pro Asn
1

<210> SEQ ID NO 55
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 55

Xaa Pro Gln
1
```

```
<210> SEQ ID NO 56
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 56

Xaa Pro Ser
1

<210> SEQ ID NO 57
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 57

Xaa Pro Pro
1

<210> SEQ ID NO 58
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 58

Xaa Pro Trp
1

<210> SEQ ID NO 59
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 59

Xaa Pro Asp
1

<210> SEQ ID NO 60
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid
```

```
<400> SEQUENCE: 60

Xaa Pro His
1

<210> SEQ ID NO 61
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 61

Xaa Pro Leu
1

<210> SEQ ID NO 62
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 62

Xaa Pro Arg
1

<210> SEQ ID NO 63
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 63

Xaa Pro Val
1

<210> SEQ ID NO 64
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 64

Xaa Pro Lys
1

<210> SEQ ID NO 65
<211> LENGTH: 3
<212> TYPE: PRT
<213> ORGANISM: Artificial Sequence
<220> FEATURE:
```

<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 65

Xaa Pro Glu
1

<210> SEQ ID NO 66
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 66

Xaa Pro Phe
1

<210> SEQ ID NO 67
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 67

Xaa Pro Ile
1

<210> SEQ ID NO 68
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 68

Xaa Pro Met
1

<210> SEQ ID NO 69
<211> LENGTH: 3
<212> TYPE: PRT
<213> ORGANISM: Artificial Sequence
<220> FEATURE:
<223> OTHER INFORMATION: Tight junction antagonist
<220> FEATURE:
<221> NAME/KEY: misc_feature
<222> LOCATION: (1)..(1)
<223> OTHER INFORMATION: Xaa may be pyroglutamic acid

<400> SEQUENCE: 69

Xaa Pro Tyr
1

```
<210> SEQ ID NO 70
<211> LENGTH: 6
<212> TYPE: PRT
<213> ORGANISM: Artificial Sequence
<220> FEATURE:
<223> OTHER INFORMATION: Tight junction antagonist

<400> SEQUENCE: 70

Phe Cys Ile Gly Arg Leu
1               5
```